United States Patent
Tur'Yan et al.

[11] Patent Number: 6,027,940
[45] Date of Patent: *Feb. 22, 2000

[54] REAGENT FOR THE DETERMINATION OF ACIDS IN OILS

[76] Inventors: Yakov Tur'Yan, 425/12 Neve Yaakov; Oleg Berezin, 14/7 Neve Yaakov; Ilya Kuselman, 114 Neve Yaakov, all of Jerusalem 97350; Shenhar Avinoam, 31 Uziel Street, Jerusalem, all of Israel

[*] Notice: This patent issued on a continued prosecution application filed under 37 CFR 1.53(d), and is subject to the twenty year patent term provisions of 35 U.S.C. 154(a)(2).

[21] Appl. No.: 08/980,066

[22] Filed: Nov. 26, 1997

Related U.S. Application Data

[63] Continuation of application No. 08/494,442, Jun. 26, 1995, abandoned.

[30] Foreign Application Priority Data

Jul. 1, 1994 [IL] Israel ........................................ 110192

[51] Int. Cl.⁷ ............................ G01N 31/16; G01N 33/26
[52] U.S. Cl. .............................. 436/163; 436/60; 436/61; 252/408.1
[58] Field of Search ................................ 422/68.1, 82.03, 422/82.02, 90, 85; 436/25, 29, 30, 39, 40, 163, 60, 61; 73/19.01, 19.11; 252/408.1

[56] References Cited

U.S. PATENT DOCUMENTS

| | | | |
|---|---|---|---|
| 3,811,837 | 5/1974 | Hoffman | 436/163 X |
| 4,575,428 | 3/1986 | Clapper et al. | 252/8.5 P |
| 4,654,309 | 3/1987 | Mlinar et al. | 436/61 |
| 4,663,076 | 5/1987 | Clapper et al. | 252/356 |
| 4,677,060 | 6/1987 | Valet et al. | 435/29 |
| 4,863,692 | 9/1989 | Plumb | 422/58 |
| 4,898,725 | 2/1990 | Hoeffkes et al. | 424/70 |
| 4,919,892 | 4/1990 | Plumb | 422/58 |
| 5,053,490 | 10/1991 | Satoh et al. | 530/362 |
| 5,204,371 | 4/1993 | Skuballa et al. | 514/530 |

FOREIGN PATENT DOCUMENTS 6-41592  2/1994  Japan.

OTHER PUBLICATIONS

Yakov I. Tur'yan et al., pH–Metric emthod for the determination of acid numbers of oils, Zhurnal Analiticheskoi Khimii, vol. 46, No. 6, pp. 1150–1158, Jun. 1991.

Yakov I. Tur'yan et al., Physicochemical verification of pH–Metric Method of determination of Acid number without performing Titrations. Aqueous Systems, Zhurnal Analiticheskoi Khimii, vol. 46, No. 5, pp. 917–925, May 1991.

*Primary Examiner*—Maureen M. Wallenhorst
*Attorney, Agent, or Firm*—Edwin D. Schindler

[57] ABSTRACT

A reagent for the acid value determination in oils. The reagent contains a tertiary amine, such as triethanolamine, in a water-alcohol mixture as solvent. Preferred is isopropanol/water. The reagent allows determinations of acid values in oils in a two phase system. The use of the reagent is based on a pH-metric technique with conditional pH-measurement before and after the addition of an oil sample to the reagent.

8 Claims, 1 Drawing Sheet

REAGENT FOR THE DETERMINATION OF ACIDS IN OILS

This is a continuation of application Ser. No. 08/494,442, filed Jun. 26, 1995, now abandoned.

FIELD OF THE INVENTION

The invention concerns methods for acid value or titratable acidity determination in vegetable and other oils. Acid value (AV) is an important characteristic of the oil quality. The AV is expressed by mg KOH necessary for titration of free acids contained in 1 g oil. The invention is based on AV determination without titration. An acid-base reagent is applied which converts a mixture of acids of an oil sample into a new system. The conversion makes it possible to use directly the pH as the analytical signal for AV evaluation. The solvent is a component of the reagent, taking into account the big influence of the solvent on the completeness of sample conversion.

BACKGROUND OF THE INVENTION

Most of national and international standards for AV determination are based on the acid-base titration techniques in the non-aqueous systems (ISO 660-1983 (E); ASTM D664-89; AOCS Ca 5a-40-1989; GOST 10858-77, 5476-80, USSR). These techniques are time—and labour consuming, difficult for automation, particulary on the industrial line. They use toxic solvents, for example: diethylether, methylisobutyl ketone and others, as well as non-aqueous titrants which are very sensitive to carbon dioxide contamination from the atmosphere.

A number of techniques for AV determination without titration have been suggested. There is the pH-metric technique in the presence of a special reagent [T.M. Lapshina et al., Zh. Anal. Khim. 46(1991), 1150], chromatographic technique [R. G. Ackman, Food Sci. Technol., N.Y., 53 (1992) 47] as well as the spectroscopic technique with solvent [A. A. Ismail et al., J. Am. Oil Chem. Soc., 70 (1993) 335] and without solvent (T. K. Blumenthal et al., Am. Oil Chemists' Soc. 84th Annual Meeting and Exposition, Anahein, Calif., Apr. 28, 1993).

The techniques without titration mentioned above are not free of certain drawbacks as well. They use toxic solvents (pH-metry, chromatography, spectroscopy with solvent), use expensive and complicated instruments (chromatography and spectroscopy). The spectroscopic technique, without solvent, is time-consuming and difficult for automation.

The technique—precursor for our invention (T. M. Lapshina et al., Zh. Anal. Khem., 46(1991), 1150) was based on the reagent (0.15–0.20 mol/L triethanolamin (TEA) in the solvent 80% diethylether+19% $C_2H_5OH$+1% $H_2O$, % Vol.) and pH-metry. An oil sample was completely dissolved in the reagent. At invariable ionic strength and large excess of TEA in comparison with the sum of the determined acids a linear dependence was observed:

$$pH' = \text{const.} - 1\ g\ N_a, \quad (1)$$

where pH' is conditional pH of the oil solution in the reagent. The conditional character of pH value is caused by the use of aqueous buffer solutions for pH-meter calibration; all pH values given below are conditional ones (pH'). The value "const." in eqn(1) is the constant value for the given ionic strength, reagent concentration and pH-sensor; $N_a$ is the number of equivalents of the determined acids per litre of the reactive mixture.

The AV value was determined on the basis of eqn(1) by the standard addition method at the condition that the standard acid was added to the reagent after the oil sample:

$$AV = \frac{56.11 \cdot N_{st} \cdot V_{st}}{m(10^{\Delta pH'} - 1)}\ \text{mg KOH/g oil}, \quad (2)$$

where 56.11 is molecular weight of KOH; $N_{st}$ and $V_{st}$ are the concentration (eq/L) and the volume (mL) of the standard acid addition respectively; m is the weight of the oil sample (g); $\Delta pH' = pH'_1 - pH'_2$; $pH'_1$ is pH of the oil solution in reagent; $pH'_2$ is pH of the previous solution after addition of the standard acid.

The drawbacks of the technique-precursor (see T. M. Lapshina et al., Zh. Anal. Khim., 46 (1991) 1150) are the following:

A) The reagent is toxic.

B) Low water concentration in the reagent causes insufficient stability in work of the pH-metric sensor with glass indicator electrode and standard aqueous reference electrode.

C) The non-aqueous base reagent is very sensitive to carbon dioxide contamination from the atmosphere because of the insoluble carbonate formation which may change the pH value of the reagent ($pH'_0$).

D) The acid solution being used as standard addition (stearic acid in chloroform) is toxic and its standardization is difficult.

E) The choice of the optimal $N_{st}$ and $V_{st}$ values depends on unknown AV value that may require repeated addition or reanalysis which prolongs the analysis.

SUMMARY OF THE INVENTION

The specific reagent of the present invention is based on a specific combination of a number of components, which are provided at certain relative percentages. The main components are a solvent comprising an alcohol and water; dissolved therein a tertiary amine.

There may be used a variety of tertiary amines, the one of choice being triethanolamine; the range of water/alcohol depends on the components, and can vary for isopropanol/water/triethanolamine between 1 to 50 percent water and from 50 to 99% isopropanol.

It is clear that the solvent system must be able to extract the acid from the oil. To this mixture there is advantageously added an inert salt, such as potassium nitrate, lithium chloride, sodium chloride and the like. With potassium nitrate the preferred concentration is in the range of about 0.01 mol/liter to about 0.03 mole/liter.

For reagent calibration there is advantageously added a suitable acid with strength not less than for acetic acid. Suitable acids are hydrochloric acid, sulfuric acid, oxalic acid, acetic acid.

When triethanolamine is used, its preferred range is between about 0.15 mol/liter to about 0.5 mole/liter. The invention is illustrated in the following with reference to certain preferred reagents and their use. These are by way of example only and it is clear that they are to be interpreted in a non-restrictive manner.

A preferred reagent consists of TEA in aqueous isopropanol as solvent.

BRIEF DESCRIPTION OF THE DRAWINGS

In the enclosed Figures, which serve to illustrate the invention.

DETAILED DESCRIPTION OF THE INVENTION

Development of the new reagent is based on the emulsifying property of TEA—water—isopropanol to form a milk-like emulsion with an oil. This property provides rapid (within a minute) quantitive extraction of the acids from an oil into the TEA+water+isopropanol phase.

A water concentration of more than 50% (vol.) in the aqueous isopropanol solvent leads to the incomplete extraction of the acid from the oil. On the other hand for stable work of the pH-metric sensor and less sensitivity to carbon dioxide contamination from the atmosphere the reagent must contain a maximum of water in the solvent. Therefore the optimal composition of the solvent is about 50% water+50% isopropanol (vol. %) A TEA concentration 0.20 mol/L generally ensures a sufficient excess of the base in comparison with the sum of the determined acids. Hence, the proposed reagent composition is about: 0.20 mol/L TEA in a solvent 50% water+50% isopropanol (vol. %).

The capability of this reagent, for acid extraction from oil, allows use the volumetric ratio of an oil sample to the reagent up to 1.1:1.0. For such ratios the acid extraction remains complete; it permits to increase the weight of the oil sample and accordingly to decrease the AV detection limit.

The condition of the constant ionic strength was reached by addition of an indifferent salt, for example, 0.02 mol/L $KNO_3$.

A correct choice of the pH'$_0$ reagent allows to increase the interval of pH' for which the linear eqn (1) pH' vs 1 g $N_a$ is justified which decreases the AV detection limit.

Figure 1:
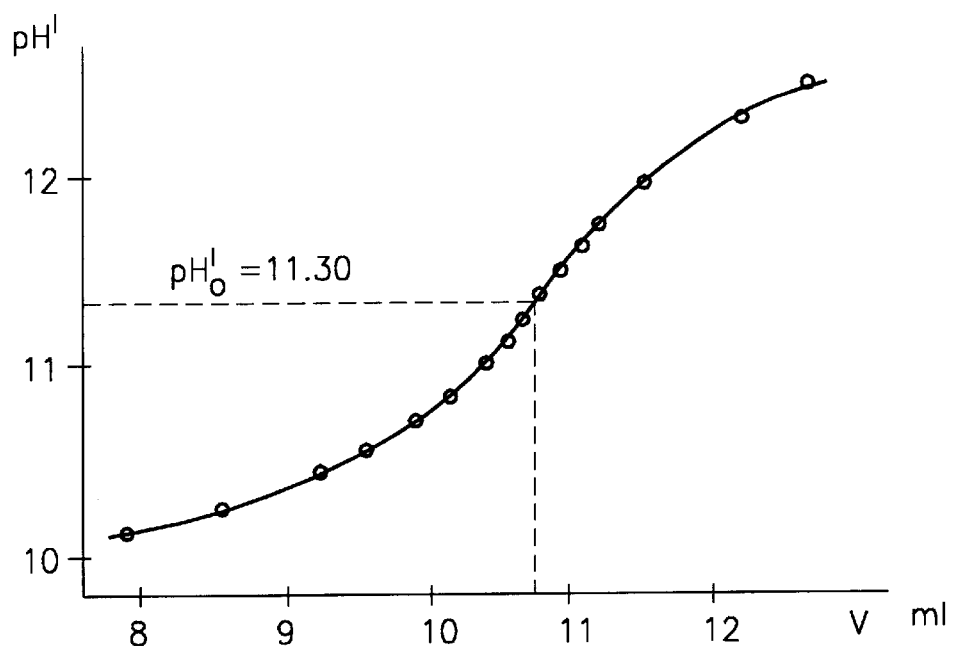
FIG. 1: The curve of titration for 50 mL HCL ($N_{HCL}$=7.70 $10^{-3}$ mol/L) in the presence of 0.20 M TEA in the solvent 50% water+50% isopropanol (% vol.). The titrant is 3.52 10 mol/L KOH.

The novel reagent enables to determine pH'$_0$ on the basis of pH-metric titration of the acid (for example, HC1) specially added to the reagent. It was shown that the pH'$_0$ value is equal to the pH' for the titration equivalence point (FIG. 1). From FIG. 1 one can see for the proposed reagent the pH'$_0$=11.30±0.05.

The reagent with pH'$_0$ is to be prepared and preserved in a hermetically closed disposable container.

The Use of the New Reagent for AV Determination in Oils

The linear dependence of pH' vs 1 g $N_a$, with the slope equal to 1.003 (r=0.999) for the new reagent (FIG. 2) allows to obtain detailed data for pH-metric AV determination in oils. For example, such data are shown in Table 1. This Table 1 was obtained by means of pH' measurements for solutions prepared by additions of aqueous standard HCl acid to 50 mL of the reagent and pH' measurements.

Table 1 presents pH' vs G, where G is mg KOH equivalent to the acids contained in 50 mL of the reagent:

$$G=56.11 \times 50 \times N_a \quad (3)$$

As an oil is practically insoluble in the proposed reagent, the volume of the reagent remains essentially constant.

TABLE 1 pH' of the reagent (0.20 mol/L TEA + 0.02 mol/L $KNO_3$ in the solvent 50% water + 50% isopropanol, % vol.; pH'$_o$ = 11.30) at different acid contents equal to G mg KOH in 50 mL of the reagent.

| pH' | G mg KOH |
|---|---|
| 9.22 | 35.05 |
| 9.23 | 34.26 |
| 9.24 | 33.49 |
| 9.25 | 32.73 |
| 9.26 | 31.99 |
| 9.27 | 31.27 |
| 9.28 | 30.56 |
| 9.29 | 29.87 |
| 9.30 | 29.20 |
| 9.31 | 28.54 |
| 9.32 | 27.90 |
| 9.33 | 27.27 |
| 9.34 | 26.65 |
| 9.35 | 26.05 |
| 9.36 | 25.46 |
| 9.37 | 24.89 |
| 9.38 | 24.33 |
| 9.39 | 23.78 |
| 9.40 | 23.24 |
| 9.41 | 22.71 |
| 9.42 | 22.20 |
| 9.43 | 21.70 |
| 9.44 | 21.21 |
| 9.45 | 20.73 |
| 9.46 | 20.26 |
| 9.47 | 19.81 |
| 9.48 | 19.36 |
| 9.49 | 18.92 |
| 9.50 | 18.49 |
| 9.51 | 18.08 |
| 9.52 | 17.67 |
| 9.53 | 17.27 |
| 9.54 | 16.88 |
| 9.55 | 16.50 |
| 9.56 | 16.13 |
| 9.57 | 15.76 |
| 9.58 | 15.41 |
| 9.59 | 15.06 |
| 9.60 | 14.72 |
| 9.61 | 14.39 |
| 9.62 | 14.06 |
| 9.63 | 13.74 |
| 9.64 | 13.43 |
| 9.65 | 13.13 |
| 9.66 | 12.83 |
| 9.67 | 12.54 |
| 9.68 | 12.26 |
| 9.69 | 11.98 |
| 9.70 | 11.71 |
| 9.71 | 11.45 |
| 9.72 | 11.19 |
| 9.73 | 10.94 |
| 9.74 | 10.69 |
| 9.75 | 10.45 |
| 9.76 | 10.21 |
| 9.77 | 9.98 |
| 9.78 | 9.76 |
| 9.79 | 9.54 |
| 9.80 | 9.32 |
| 9.81 | 9.11 |
| 9.82 | 8.91 |
| 9.83 | 8.71 |
| 9.84 | 8.51 |
| 9.85 | 8.32 |
| 9.86 | 8.13 |
| 9.87 | 7.95 |
| 9.88 | 7.77 |
| 9.89 | 7.59 |
| 9.90 | 7.42 |
| 9.91 | 7.25 |
| 9.92 | 7.09 |
| 9.93 | 6.93 |

TABLE 1-continued pH' of the reagent (0.20 mol/L TEA + 0.02 mol/L KNO$_3$ in the solvent 50% water + 50% isopropanol, % vol.; pH'$_o$ = 11.30) at different acid contents equal to G mg KOH in 50 mL of the reagent.

| pH' | G mg KOH |
|---|---|
| 9.94 | 6.77 |
| 9.95 | 6.62 |
| 9.96 | 6.47 |
| 9.97 | 6.32 |
| 9.98 | 6.18 |
| 9.99 | 6.04 |
| 10.00 | 5.90 |
| 10.01 | 5.77 |
| 10.02 | 5.64 |
| 10.03 | 5.51 |
| 10.04 | 5.39 |
| 10.05 | 5.27 |
| 10.06 | 5.15 |
| 10.07 | 5.03 |
| 10.08 | 4.92 |
| 10.09 | 4.81 |
| 10.10 | 4.70 |
| 10.11 | 4.59 |
| 10.12 | 4.49 |
| 10.13 | 4.39 |
| 10.14 | 4.29 |
| 10.15 | 4.19 |
| 10.16 | 4.10 |
| 10.17 | 4.01 |
| 10.18 | 3.91 |
| 10.19 | 3.83 |
| 10.20 | 3.74 |
| 10.21 | 3.66 |
| 10.22 | 3.57 |
| 10.23 | 3.49 |
| 10.24 | 3.41 |
| 10.25 | 3.34 |
| 10.26 | 3.26 |
| 10.27 | 3.19 |
| 10.28 | 3.12 |
| 10.29 | 3.05 |
| 10.30 | 2.98 |
| 10.31 | 2.91 |
| 10.32 | 2.84 |
| 10.33 | 2.78 |
| 10.34 | 2.72 |
| 10.35 | 2.66 |
| 10.36 | 2.60 |
| 10.37 | 2.54 |
| 10.38 | 2.48 |
| 10.39 | 2.42 |
| 10.40 | 2.37 |
| 10.41 | 2.32 |
| 10.42 | 2.26 |
| 10.43 | 2.21 |
| 10.44 | 2.16 |
| 10.45 | 2.11 |
| 10.46 | 2.07 |
| 10.47 | 2.02 |
| 10.48 | 1.97 |
| 10.49 | 1.93 |
| 10.50 | 1.89 |
| 10.51 | 1.84 |
| 10.52 | 1.80 |
| 10.53 | 1.76 |
| 10.54 | 1.72 |
| 10.55 | 1.68 |
| 10.56 | 1.64 |
| 10.57 | 1.61 |
| 10.58 | 1.57 |
| 10.59 | 1.53 |
| 10.60 | 1.50 |
| 10.61 | 1.47 |
| 10.62 | 1.43 |
| 10.63 | 1.40 |

Hence, the G value obtained from Table 1 allows to calculate AV for the weight m of the oil sample added to 50 mL of the reagent.

$$AV = \frac{G}{m} \text{ mg KOH/g oil} \tag{4}$$

Figure 2:
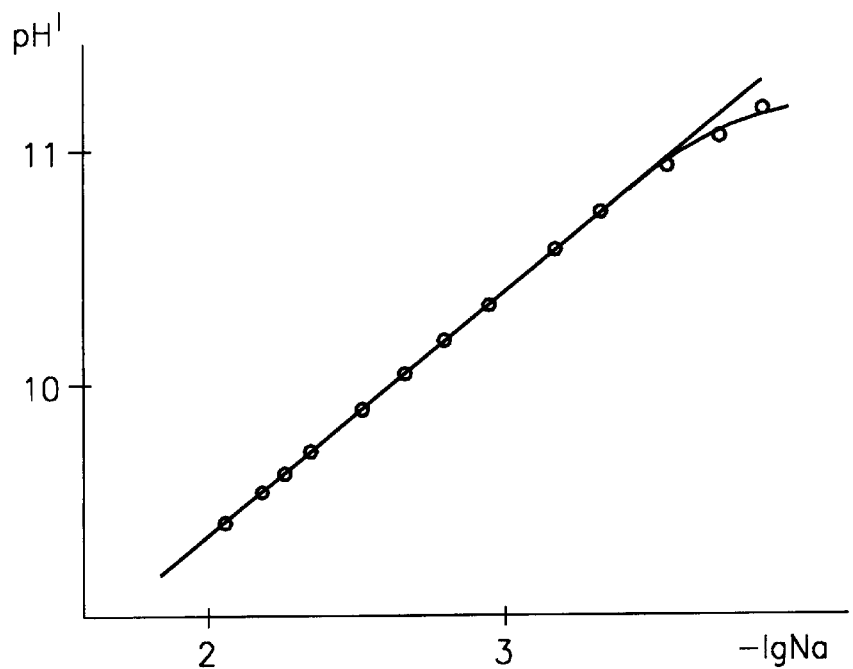
FIG. 2: Dependence pH' vs 1 g $N_a$. Reagent 0.20 mol/L TEA+0.02 mol/L $KNO_3$ in solvent 50% water and 50% isopropanol, % vol. (pH'$_0$=11.30). ($N_a)_{min}$=4.99 $10^{-4}$, mol/L is the low limit of $N_a$ for linear dependence pH' vs. 1 g $N_a$ (pH'=10.63).

The values pH's$\leq$10.63 in Table 1 correspond to the $N_a \geq 5.10^{-4}$ eq/L by linear dependence pH' vs 1 g $N_a$ with slope equal to 1 demonstrated on FIG. 2. The $(N_a)_{min}$ value from linear dependence pH' vs 1 g $N_a$ enables to calculate the detection limit for AV ($AV_{lim}$) by standard addition method or by Table 1. For example for m=(40–50)g of the oil sample and 50 mL of the reagent $AV_{lim}=3.10^{-2}$ mg KOH/g oil.

It was proposed to use a control solution for possible correction of the result of pH' measurement for AV determination by Table 1. Such correction is necessary when analysis conditions (temperature and in the pH-sensor characteristics) differ from the conditions of measurement used for obtaining Table 1. For this purpose a definite amount of an acid, for example, aqueous standard solution of HCl is added to the reagent with pH'$_0$. The concentration $N_a$ of HCl in the reagent must be within the internal $5.10^{-4}$–$5.10^{-3}$ eq/L.

This correction is carried out as follows. The pH'$_c$ value for the control solution is measured. By the G value (eqn.(3)) for the control solution from Table 2 the corresponding pH' value is found. The difference $$\delta = pH'_c - pH' \tag{5}$$

is used as a correction to the result of the pH measurement for the oil sample in the reagent (pH')$_s$. Corrected pH is $$(pH')_{corr} = (pH')_s + \delta \tag{6}$$

By the (pH')$_{corr}$ the G value is obtained from Table 1 and afterwards the AV for the analyzed sample may be found by eqn. (4). For example, the result of pH measurement for the control solution is pH'$_c$=9.76 at G=9.32 mg KOH. The value G=9.32 mg KOH corresponds to pH'=9.80 from Table 1. Hence, the $\delta$=−0.04 by eqn. (5). For oil sample with m=2.731 g in the reagent (pH')$_s$=10.24 was obtained. From this the (pH')$_{corr}$=10.20 by eqn. (6), from Table 1, G=3.74 mg KOH and AV=1.37 mg KOH/g oil by eqn. (4). The most important advantage of Table 1 usage is acceleration of the analysis down to 1–2 min. The control solution mentioned above may be also used for pH-metric AV determination in oils directly. For this purpose the pH'$_c$ of the control solution with a known volume ($V_c$,mL) is to be measured. An oil sample with the weight (m) is to be added to the control solution and the pH'$_2$ should be measured. The equation for AV calculation has the form:

$$AV = \frac{56.11 \cdot N_a \cdot V_c}{m}(10^{\Delta pH'} - 1) \text{ mg KOH/g oil,} \tag{7}$$

where pH'=pH'$_c$−pH'$_2$; $N_a$ is the acids concentration in the control solution (eq/L).

The important advantage of this use of control solution for pH-metric AV determination in oils is decreasing of sensitivity to carbon dioxide contamination from the atmosphere because of acidification of the solution.

Precision and Accuracy of the Results

Precision and accuracy of the results of AV determination with the use of the novel reagent are the same or higher than those for the technique-precursor (see the data published in T. M. Lapshina et al., Zh. Anal. Khem, 46 (1991) 1150) and slightly lower than those for the standard titration technique (ISO 660–1983 (E)) on condition that the precision of pH measurements is not less than ±0.01 (see Table 2).

In Table 2 there are shown the average results obtained by standard titration (ISO 660–1983 (E)) and the novel technique from n=5 replicates (parallel determinations) for each $-\overline{AV}_s$ and $\overline{AV}_p$, respectively; standard deviations for these replicates–$S_s$ and $S_p$, respectively; $F=S^2_p/S^2_s$ and $t=\overline{AV}_s - \overline{AV}_p/[S^2_{s+s}{}^2_p)/5]$. The details of the experiments are described below (in "Examples").

The critical values for F-ratio is 6.39 at the 5% level of significance and the number of degrees of freedom n−1=4. For t-ratio the critical value is 2.31 at the 5% level of significance and the number of degrees of freedom 2(n−1)=8. From comparison of the F-data with the critical value it follows that differences between precision of results obtained by standard titration and proposed technique are insignificant (all F are less than 6.39). The accuracy for these techniques is approximately the same so far as the deviations of the average AV results obtained by proposed technique from the average results obtained by the standard technique are insignificant in comparison with random errors (all t are less than 2.31).

The precision and accuracy obtained by pH-metric technique proposed ate sufficient for quality control in industry.

TABLE 2

Comparison of AV determination results by standard titration technique ISO 660–1983 (E) and those obtained by the novel.

|  |  | Standard titration | | Novel technique | | | |
| --- | --- | --- | --- | --- | --- | --- | --- |
| No. | Oil | $\overline{AV}_s$ | $S_s$ | $\overline{AV}_p$ | $S_p$ | F | t |
| 1 | Olive | 3.69 | 0.05 | 3.68 | 0.09 | 3.24 | 0.22 |
| 2 | Model | 22.3 | 0.27 | 22.4 | 0.49 | 3.29 | 0.40 |
| 3 | Model | 0.153 | 0.003 | 0.151 | 0.006 | 4.00 | 0.67 |
| 4 | Corn | 0.104 | 0.004 | 0.106 | 0.007 | 3.06 | 0.55 |

EXAMPLES

AV values of commercial vegetable oils such as olive, corn and soya oil were determined. Since the interval of AV values in these oils is relatively small (0.2–4.0 mg KOH/g oil), we prepared vegetable oil models in a wide range of AV: from 0.15 to 22 mg KOH/g oil. To prepare the models oleic acid was dissolved in soya oil.

The AV in the oil samples were first determined by standard potentiometric titration (ISO 660–1983 (E)), the results were accepted as correct. The 672 Metrohm titroprocessor with glass electrode 6.0133.100 and aqueous reference electrode 6.0726.110 were used for the standard titration. A weighed oil sample was added to methyl-isobutyl keton, and this solution was titrated by standardized KOH solution $5.00 \cdot 10^{-2}$ mol/L in isopropanol (carbonate free). Values of $\overline{AV}_s$ were obtained as the average value for 5 titrations-replicates. Values $S_s$ were calculated from the same data (Table 2). The same oil samples were used for AV determination by the novel pH-metric technique (Examples 1–5). The titro-processor and pH-sensor (the precision of pH measurements is ±0.01) were the same as those used for the titration. Values $\overline{AV}_p$ were obtained as average value for 5 pH-metric measurements-replicates each, simultaneously with $S_p$ (Table 2). The following reagents were applied in examples 1–5:

Reagent No. 1:
0.20 mol/L TEA+0.02 mol/L $KNO_3$ in the solvent 50% water+50% isopropanol, vol. %, pH'$_0$=11.30.

Reagent No. 2:
(control solution) 0.20 mol/L TEA+0.02 mol/L $KNO_3$+ $4.00 \cdot 10^{-3}$ mol/L HCl in the solvent 50% water+50% isopropanol, vol. %.

Reagent No. 3:
(control solution) 0.20 mol/L TEA+0.02 mol/L $KNO_3$+ $9.90 \cdot 10^{-4}$ mol/L HCl in the solvent 50% water+50% isopropanol, vol. %.

Example 1

To determine AV on the basis of Table 1 a weighted oil (model No. 2, Table 2), m=0.507 g was added to the reagent No. 1. After 1–2 min of the mixture being stirred, pH'=9.71 was measured. On the pH' basis G=11.45 mg KOH was obtained from Table 1 and AV=22.6 mg KOH/g oil was calculated (eqn. (4)). The values of $\overline{AV}_p$ and $S_p$ are given in Table 2.

Example 2

In this example the reagent No. 2 was used for AV determination in the same oil as in Example 1 (model No. 2, Table 2). Addition of the weighted oil sample m=1.510 g to 50 mL of stirred reagent was carried out. The following pH' values were obtained: pH'$_c$=9.66 before the oil addition and pH'$_2$=9.05 after the oil addition. AV was calculated by eqn. (7): AV=22.8 mg KOH/g oil. The values of $\overline{AV}_p$ and $S_p$ are given in Table 2.

Example 3

Reagent No. 1 was used for AV determination in olive oil (sample No. 1, Table 2). In this example the AV was also found with the aid of the standard addition method (eqn. (2)). For m=2.439 g of olive oil the following pH' values were obtained: pH'$_1$=9.62 and pH'$_2$=9.27 ($V_{st}$=0.2 mL, $N_{st}$= 1.0 eq/L HCl) Hence, AV=3.71 mg KOH/g oil. The values $\overline{AV}_p$ and $S_p$ are given in Table 2.

Example 4

The model No. 3 (Table 2) was added to 50 mL of the reagent No. 3. For m=26.965 g the following pH' values were obtained: pH'$_c$=10.20, pH'$_2$=9.80. Hence from (eqn. (7)) AV=0.156 mg KOH/g oil. The values $\overline{AV}_p$ and $S_p$ are given in Table 2.

Example 5

To determine AV on the basis of Table 1 a weighted sample of corn oil (sample No. 4, Table 3) m=31.647 g was added to 50 ml of the reagent No. 1. After 1–2 min of the mixture being stirred pH'=10.24 was measured. On the basis pH' the value G=3.41 mg KOH was obtained from Table 1 and AV=0.108 mg KOH/g oil was calculated by eqn. 4. The values $\overline{AV}_p$ and $S_p$ are given in Table 2.

Advantages of the Novel Reagent and Its Use

A) The reagent is non-toxic.

B) The reagent allows to carry out the analysis in a two-phase system "oil-reagent" that enables to increase considerably the weight of the analyzed oil sample and to decrease the AV detection limit.

C) Due to high water content (50%, vol.) the reagent ensures stability in work of the pH-metric sensor and besides this such reagent is less sensitive to carbon dioxide contamination from the atmosphere.

D) In comparison with the technique-precursor (T. M. Lapshina et al., Zh. Anal, Khim, 46 (1991) 1150), in the novel technique acid addition to the reagent (the control solution) is carried out before oil sample addition, which also decreases the contamination of the reagent by carbon dioxide from the atmosphere.

E) The novel technique is simple and fast.

F) The new technique use reduces the time—and labor—consumption in comparison with standard titration techniques.

G) Cheaper instruments are used, in comparison with titroprocessors.

H) Automation is easier in comparison with standard titration techniques.

We claim:

1. A reagent for pH-metric acid value determination in oils, comprising 0.15 to 0.5 mol/L triethanolamine, an inert salt and an alkali in a mixture of water and isopropanol, wherein the alkali has a concentration corresponding to an optimal conditional $pH'_0$ value of the reagent said $pH'_0$ value being that of an equivalence point on a pH metric titration curve of a strong acid added to a test portion of said reagent during its preparation, prior to the addition of the alkali, said strong acid being selected from the group consisting of hydrochloric acid and sulfuric acid.

2. The reagent according to claim 1, wherein said inert salt is selected from the group consisting of potassium nitrate, lithium chloride and sodium chloride, said inert salt being present in a concentration in the range of from 0.01 to 0.03 mol/L.

3. A reagent for pH-metric acid value determination in oils according to claim 1, wherein the ratio of water and isopropanol in the mixture of water and isopropanol is sufficient for providing a complete extraction of acids from an oil into said reagent.

4. The reagent according to claim 3, wherein isopropanol is at a concentration from 50% to 99% by volume.

5. The reagent according to claim 3, wherein said inert salt is selected from the group consisting of potassium nitrate, lithium chloride and sodium chloride, said inert salt being present in a concentration in the range of from 0.01 to 0.03 mol/L.

6. The reagent according to claim 3, wherein said alkali is potassium hydroxide.

7. The reagent according to claim 1, wherein the concentration of water is from 1 to 50%, by volume, and the concentration of isopropanol is from 50 to 99%, by volume.

8. The reagent according to claim 1, wherein the alkali is selected from the group consisting of potassium hydroxide, lithium hydroxide and sodium hydroxide.

* * * * *